United States Patent [19]

Wang

[11] Patent Number: 4,760,272
[45] Date of Patent: Jul. 26, 1988

[54] OPTICAL PRECIPITATION DETECTION AND IDENTIFICATION SYSTEM USING SCINTILLATION DETECTION

[75] Inventor: Ting-I Wang, Gaithersburg, Md.

[73] Assignee: Scientific Technology, Inc., Rockville, Md.

[21] Appl. No.: 1,459

[22] Filed: Jan. 8, 1987

[51] Int. Cl.⁴ .................... G01N 15/06; G01N 15/07
[52] U.S. Cl. ..................................... 250/573; 340/583
[58] Field of Search .................... 250/222.2, 338, 573; 356/442; 340/583

[56] References Cited

U.S. PATENT DOCUMENTS

| | | | |
|---|---|---|---|
| 4,432,649 | 2/1984 | Krause | 250/573 |
| 4,647,780 | 3/1987 | Dunkel | 250/573 |
| 4,690,553 | 9/1987 | Fukamizu et al. | 340/583 |

OTHER PUBLICATIONS

"A Feasibility Study of Identifying Weather by Laser Forward Scattering" by K. B. Earnshaw, et al, Journal of Applied Meteorology, vol. 17, No. 10, Oct. 1978.
"Laser Weather Identified: Present and Future", by Ting-I Wang, et al, Journal of Applied Meteorology, vol. 21, No. 11, Nov. 1982.
"An Optical Velocimeter for Precipitation", by Ting-I Wang, et al, presented at the Topical Meeting on Optical Propagation Through Turbulence, Rain and Fog, Boulder, Colorado, Aug. 9-11, 1977.

Primary Examiner—David C. Nelms
Assistant Examiner—William L. Oen
Attorney, Agent, or Firm—Charles H. Thomas

[57] ABSTRACT

A weather identification system is provided for remotely detecting precipitation and for determining the nature of precipitation in an open environment, as at an aircraft landing field. The system employs an optical transmitter and receiver, wherein particles of precipitation passing through a light beam from the transmitter cause scintillations which are detected at the receiver. A drastic reduction in spatial separation between the light transmitter and receiver makes possible the use of a partially coherent light beam in place of a conventional laser beam. The transmitter and receiver are spaced apart a distance of approximately one meter, and the product of one half of the angle of incoherency multiplied by the spatial separation between the transmitter and receiver is no greater than about 2.5 millimeters. Rain passing through the light beam produces scintillations with substantial frequency components above one kilohertz. Snow induced frequencies are primarily below a few hundred hertz. The receiver is coupled to an automatic gain control means and a signal processor. By measuring the spectrum energy in various frequency bands, and by comparing the ratios of the measurements, the existence of precipitation may be ascertained and the type of precipitation can be identified remotely.

16 Claims, 5 Drawing Sheets

OPTICAL PRECIPITATION DETECTION AND IDENTIFICATION SYSTEM USING SCINTILLATION DETECTION

BACKGROUND OF THE INVENTION

1. Field of the Invention

The present invention relates to a system for optically and electronically ascertaining the existence of precipitation and the nature of precipitation in ambient air from a remote location.

2. Description of the Prior Art

Automatic weather identification systems have previously been devised which employ laser scintillations and scattering. The purpose for such automatic weather identification is to provide for remote monitoring of weather without the necessity for human observation at the weather monitoring site. Such a technique allows precipitation conditions at unmanned airfields to be remotely monitored and reported to aircraft in flight.

The nature of precipitation can be ascertained by observing the effects of precipitation on visible and infrared wave transmissions through the atmosphere. A determination of the existence and nature of precipitation in the atmosphere can be performed by observing the increase in high frequency components caused by the fine interference patterns as falling particles of precipitation sweep past a horizontally oriented line apertured light detector. The advantage of using a horizontally oriented line apertured light detector is that it is sensitive only to the vertical motion of the falling precipitation particles. Rain induced scintillations contain substantial frequency components above one kilohertz. Snow induced frequencies are primarily below a few hundred hertz.

Conventional optical weather monitoring systems employ optical transmitters that have all relied upon sources of coherent light, typically laser beams, which require an extremely large distance of light transmission in order to obtain a statistically significant sampling of precipitation so as to ascertain the rate of precipitation. The necessary spatial separation between the receiver and the transmitter of such laser scintillation detection systems is on the order of fifty meters. This large spatial separation between the transmitter and receiver of a weather monitoring system is inconvenient for use in field operation, such as at airports, due to the large area which is required to effectuate automated monitoring. Furthermore, such conventional systems are subject to considerable contamination as a result of air turbulence which is likely to occur in ambient air over a distance of fifty meters. As a result, automated systems which have heretofore been implemented to replace human judgment have been utilized to only a very limited degree. Also, most other types of conventional automated weather monitoring systems can only measure total water content of precipitation in ambient air, and are unable to identify the type of precipitation, as between rain, snow or hail, without assistance from human observers.

SUMMARY OF THE INVENTION

The present invention is based upon the realization that the correct identification of different types of precipitation is possible in a near field region which involves transmission of a partially coherent light source over a path length which is much shorter than that of conventional optical systems. According to the present invention, a partially coherent source, such as an infrared light emitting diode, may be used in place of the laser source which conventional optical weather identification systems have required. A light emitting diode has the advantage of being more reliable over a laser source. Also, there are no safety regulations governing radiation hazards of a light emitting diode. A light emitting diode is also much more economical than a laser source.

Due to the variable frequency of electromagnetic radiation from a partially coherent light transmission source, part of the precipitation induced optical scintillation detected by a receiver will be smeared. Larger angular incoherency of a light source results in lower scintillation frequency components because a larger angular incoherency projects a larger shadow on the receiving plane and hence produces signals of lower frequency. Because high frequency components of rain drop induced scintillations are critical for discriminating between rain and snow, a half angle of incoherency which is too large may result in insufficient amounts of usable signals in the high frequency band. For all practical purposes, therefore, the product of one-half the angle of incoherency of the tranmitter, as measured in radians, multiplied by the distance of separation of the transmitter and the receiver, must be no greater than about 2.5 millimeters.

The percentage light intensity fluctuations (scintillation indices) detected by the optical receiver within certain frequency ranges are indicative both of the existence of precipitation and the nature of detected precipitation. Frequency components above one kilohertz are indicative of rain. Snow induced frequencies are primarily below a few hundred hertz. Accordingly, electronic signals generated from the received scintillations are directed to three different band pass filters to quantify scintillations in low, mid and high frequencies ranges. The low and high frequencies correspond to snow and rain, respectively. The mid frequency range provides further information on discriminating rain and snow. The low frequency band may be from 25 hertz to 250 hertz, for example. The medium band may be from 250 hertz to 1,000 hertz, or one kilohertz. The high band may extend from 1 kilohertz to 4 kilohertz.

The high frequency band is used for detecting the existence of precipitation. That is, measurements in the high band are indicative of whether or not precipitation exists at all. The ratio of the amount of scintillations in the high band to the amount in the low band is used to discriminate between rain and snow. Rain is indicated when the ratio of scintillations in the high band to the low band is great. Conversely, snow is indicated where the ratio of scintillations in the high band to the low band is small. For melting snow the spectrum is close to that of rain, and occasional ambiguity may result. The mid (or high) band gives quantitative measurement of rainfall rates whereas the low band gives snow intensities. In addition to the three channels of frequency discrimination, the signal processor coupled to the receiver also provides a monitored channel of signal strength to detect accidental blocking of the beam or failure of the light source.

In one broad aspect the present invention may be considered to be a weather condition indicating system comprising a partially coherent light beam generating transmitter and an optical receiver located in optical communication with the transmitter and in spaced separation therefrom. The light source and distance of separation are such that the product of one-half the angle of incoherency of the light beam, as measured in radians, multiplied by the distance of separation of the transmitter and receiver is no greater than about 2.5 millimeters. The weather condition identification system is also comprised of automatic gain control means coupled to amplify signals from the receiver that are generated in response to scintillations occurring in the light beam from the transmitter. Also, a signal processing means is provided for separately isolating signals from the receiver having frequencies characteristic of rain and snow. These may be considered to be first, second and third outputs of detected scintillations. The first output has a frequency range characteristic of rain. The second output has a frequency range lower than that of the first output and characteristic of rain and/or snow. The third output has a frequency range lower than both said first and second outputs and characteristic of snow. For demarkation purposes, the first output may be above about one kilohertz. The second output may be between about 250 hertz and about 1 kilohertz, and the third output may be below 250 hertz. The scintillation indices measured at all three outputs may be used to identify precipitation occurrences (yes/no) The ratios of the three outputs may be used to discriminate rain aginst snow.

A precipitation sensing system can be designed with a very short length, on the order of one meter. Also, a partially coherent source such as an infrared light emitting diode (IRED) may be used. An IRED is more reliable than a coherent source, such as a laser. However, a partially coherent source will also smear out part of the precipitation generated optical scintillation. This kind of smearing will change the frequency composition of the detected scintillation at the receiving plane. Even so, an IRED may be used to obtain the proper identification of signatures of different types of precipitation.

An IRED driver provides an electrical square wave pulse to drive the IRED light source. The light from the IRED is transmitted through a focusing lens to a receiver across a spatial separation on the order of one meter. The light received by the receiver is transmitted through a horizontal, line aperture in another lens to a photosensitive diode. The photosensitive diode is coupled to a demodulating system, which in turn is coupled to a spectrum analyzer An analysis of the frequency detected by the spectrum analyzer is indicative of whether precipitation is present between the transmitter and receiver, and if so, whether that precipitation is rain or snow.

The invention may be described with greater clarity and particularity by reference to the accompanying drawings.

DESCRIPTION OF THE DRAWINGS

FIG. 9 illustrates the power connections to certain of the operational amplifiers depicted in FIGS. 5-8.

FIG. 10 illustrates the power connections to other of the operational amplifiers depicted in FIGS. 5-8.

FIG. 11 is a diagram illustrating operation of the lens heating system of the embodiment of FIG. 1.

DESCRIPTION OF THE EMBODIMENT

Figure 1:
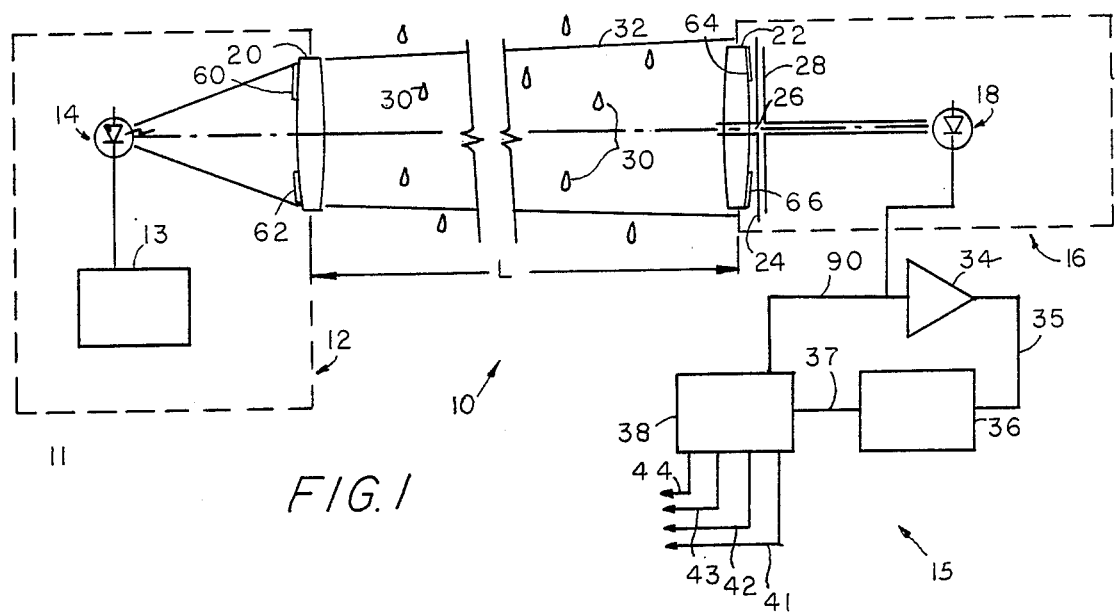
FIG. 1 is a functional block diagram of a preferred embodiment of a weather identification system according to the invention.

FIG. 1 is a functional block diagram illustrating a weather identification system indicated generally at 10. The weather identification system 10 includes a transmitter 11 and a receiver 15. The transmitter 11 includes both a power supply (not depicted) and a partially coherent light beam source indicated generally at 12 and employing an infrared light emitting diode (IRED) 14. The transmitter 11 includes an IRED modulator 13 which drives the IRED 14. Within the receiver of the system 10 a photosensitive receiver means is indicated generally at 16, and employs a PIN photodiode 18. The light beam source 12 of the transmitter 11 includes a 175 millimeter achromatic transmitter focusing lens 20 having a focal ratio of F3.5. The receiver means 16 likewise includes a receiver lens 22, identical to the lens 20, and a mask 24 which defines a horizontal slot 26 one millimeter in height and which is located behind the receiver lens 22. An infrared filter 28 is located behind the mask 24.

The photosensitive receiver means 16 is positioned a predetermined distance from the partially coherent light beam source 12 and in optical communication therewith. The receiver 16 produces electronic signals in response to the movement of particles, such as the precipitation particles indicated at 30, through the infrared beam 32 directed from the source 12 toward the receiver 16. The precipitation particles cause scintillations in the infrared beam 32 as they pass between the light beam source 12 and the receiver 16. The predetermined distance of spatial separation is indicated by the distance L. The product of the predetermined distance L and one-half the angle of incoherency of the partially coherent light beam source 12, as measured in radians, must be no greater than about 2.5 millimeters. In the preferred embodiment of the invention illustrated, this product is about 1.1 millimeters and the spatial separation L of the transmitter and the receiver is about one meter. The transmitter focusing lens 20 produces a partially coherent light beam 32 about 50 millimeters in diameter.

The weather identification system 10 also includes an automatic gain control means or receiver 36 and a signal processor 38 for producing first, second and third separate outputs 41, 42 and 43 respectively for detected frequencies. The first output 41 is indicative of signals of frequencies of between about 1 kilohertz to 4 kilohertz. The second output 42 is indicative of frequencies of between about 250 hertz and 1 kilohertz. The third output 43 is indicative of signals of frequencies below about 250 hertz. In the preferred embodiment the signal processor 38 also provides a fourth output 44 which serves as a channel for monitoring the signal strength from the transmitter 11 to the receiver 15. The output 44 provides an alert to any accidental beam blocking or failure of the light source 12.

A signal on the output 41 above a predetermined threshold is indicative of the existence of precipitation passing through the light beam 32. The ratio of the strength of the output 41 to that of the output 43 is indicative of whether the precipitation detected is rain or snow. The output 42 gives more detailed information to discriminate rain against snow. In the preferred embodiment of the invention illustrated, the system also includes a preamplifier 34 coupled between the photodiode 18 and the automatic gain control receiver 36.

Figure 2:
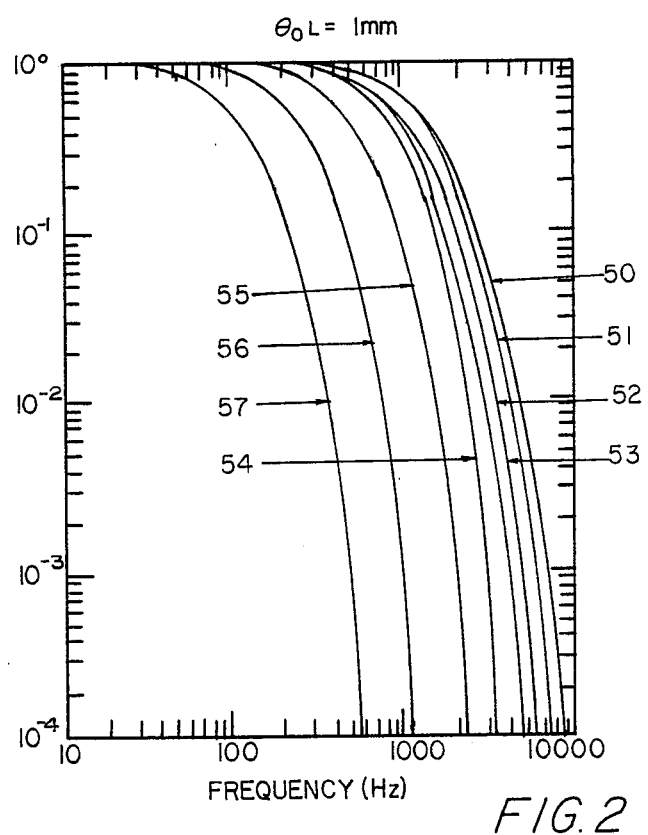
FIG. 2 is a logrithmic graph of the temporal power spectrum for different types and rates of precipitation using the embodiment of the invention of FIG. 1.

FIG. 2 illustrates the temporal power spectra produced by the weather identification system 10 for different rain and snow rates. FIG. 2 is a logrithmic graph, the abscissa of which is the frequency of scintillations measured in hertz and the ordinate of which is the precipitation induced temporal power spectrum. The graph of FIG. 2 is illustrative of scintillations produced in the system 10 of FIG. 1 where the product of the distance L and one half the angle of incoherency of the partially coherent light beam source 2 measured in radians is about one millimeter. The plot lines 50 through 53 are plots of scintillations resulting from different rates of rain. The rain rates associated with these plot lines are measured in millimeters per hour and are set forth in Table 1.

The plot lines 55 through 57 for scintillations produced by snow are at lower frequencies than the rain plot lines 50 through 53. The plot line 54 represents scintillations from melting snow, while the plot line 55 represents scintillations from fast snow. The plot line 56 illustrates scintillations from a medium snow while the plot line 57 is indicative of a slow snow. The minus 10 decibel cut off frequencies are 260 hertz, 520 hertz and 1040 hertz for slow, medium and fast snow respectively. All of these cut off frequencies are substantially lower than the 2,000 hertz cut off frequencies for the plot lines 50-53 of the rain spectrum. Therefore, rain and snow can be separately identified by discriminating between the plot lines 50-53 and the plot lines 55-57. The melting snow plot line 54 is close to that of rain, and may cause occasional ambiguity in identification.

One major concern of the system design is that the signal detected by the receiver means 16 of FIG. 1 must have a sufficient signal to noise ratio under various background lighting conditions. Background light contamination is present from natural ambient lighting conditions, such as sunshine, as well as man made lighting conditions such as street lighting, flood lighting and the like. The infrared light emitting diode 14 is therefore driven by the modulator 13 to insure that the system is immune to background noise.

The carrier frequency generated by the modulator 13 must be much higher than the frequency band of interest. From FIG. 2 it is evident that the precipitate induced scintillation spectra clearly indicate that very limited energy lies above 5 kilohertz. Therefore, a carrier frequency of at least 10 kilohertz and preferably 50 kilohertz is generated by the IRED modulator 13. To efficiently drive the IRED 14, 50% duty cycle square wave modulation is employed.

As hereinbefore noted, the infrared light emitted from the IRED 14 is collected by the focusing lens 20 to form a partially coherent light beam 32 about 50 millimeters in diameter. The light beam 32 is pointed toward the receiving lens 22 of the receiver 16 which is located about one meter from the transmitting lens 20. The precipitation particles 30 falling through the beam 32 will modulate the beam to cause scintillations in the received light signal. The optical assembly of the receiver means 16 employs the mask 24 having the horizontal line aperture 26 so as to gain sensitivity to the vertical motion of the precipitation particles 30 as they pass through the beam 32. The modulated light from the transmitter 11 is detected by the PIN photodiode 18 which is coupled to the preamplifier 34 and the automatic gain controlled receiver 36. The automatic gain controlled receiver 36 acts as a normalizer to overcome the problems associated with received power fluctuations caused by temperature change, component aging, dust on the lenses 20 and 22 and the obscuring effects of fog or haze. The output of the automatic gain controlled receiver 36 is demodulated and passed to the signal processor 38. If desired, the output of the automatic gain controlled receiver 36 can be coupled through a parallel connection for recordation on magnetic tape for later processing.

The temporal frequency spectrum of the induced scintillations varies according to the size and velocity of the falling precipitation. By measuring the spectrum energy in various frequency bands and comparing their ratios, the existence of precipitation, as opposed to the lack thereof, and the type of precipitation, as between rain and snow, can be identified. Also, turbulence combined with a temperature gradient will also produce scintillation of the optical beam as well. It is very important for the weather identification system 10 to be able to identify weather induced signals in the presence of turbulence induced signals.

The preferred embodiment of the weather identification system 10 is able to provide greater suppression of turbulence contamination, of the order of 20 decibels, as contrasted with a conventional, long base line system utilizing a coherent light source. Nevertheless, turbulence contamination cannot be ignored in the weather identification system 10. From FIG. 2 it is evident that rain induced scintillations contain substantial frequency components above one kilohertz. Snow induced scintillations contain frequencies below a few hundred hertz. Therefore, in the preferred embodiment 10 of the weather identification system of the invention, the three frequency bands of the scintillation spectrum produced as outputs are:

High band 41—1 kilohertz to 4 kilohertz.
Medium band 42—250 hertz to 1,000 hertz
Low band 43—25 hertz to 250 hertz The weather identification system 10 is physically comprised of separate transmitter and receiver modules, respectively mounted on a "U" shaped arm. All of the associated electronics, including power supplies, the IRED modulator 13, the automatic gain controlled receiver 36, the signal processor 38, and any optional lightning protection devices are housed in an all-weather proof enclosure.

Figure 4:
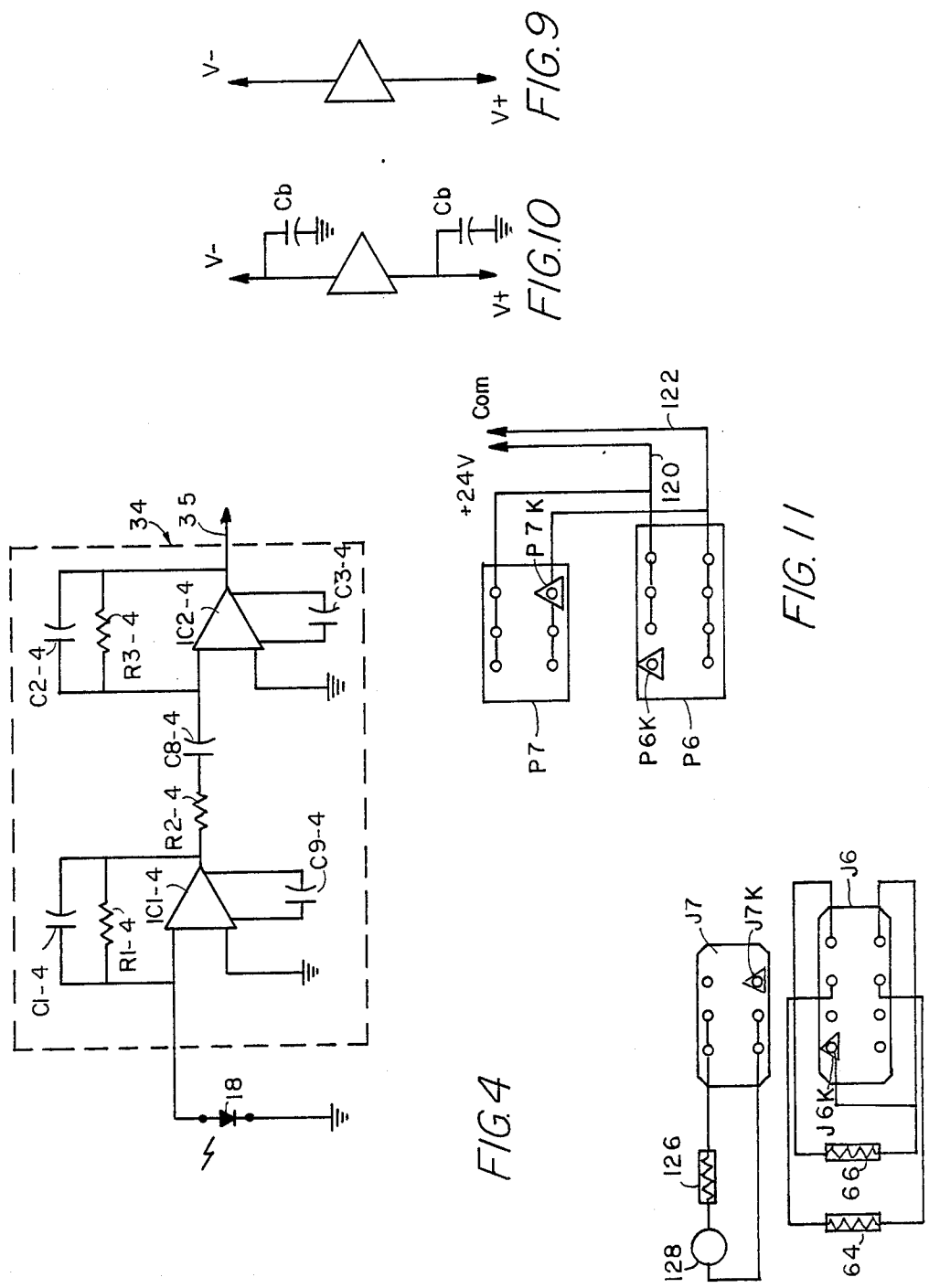
FIG. 4 is a schematic diagram of the preamplifier.

Because the transmitter light source 12 and the photosensitive receiver module 16 are exposed to ambient weather conditions, it is extremely important to the proper operation of the system for both of the lenses 20 and 22 to be free of condensed water and frost. For this purpose, thermofoil heaters are bonded to the inside of each lens. The transmitter heaters are indicated at 60 and 62 and the receiver heaters are indicated at 64 and 66. Since light is transmitted through the receiver lens 22 only through the narrow horizontal slot 26, the heaters 64 and 66 can cover all but a half inch horizontal strip through the center of each of the lenses 20 and 22. To evenly heat each lens, the means for lens heating is comprised of a pair of heaters, as illustrated in FIGS. 1 and 4. The heater 60 for the transmitting lens 20 is located above the clear area of that lens, while the heater 62 is located below the clear area. Likewise, the heater 64 for the receiving lens 22 is located above the clear area, while the heater 66 is located below the clear area.

Each of the heaters 60–64 has a nominal resistance of 240 ohms. The transmitting lens heaters 60 and 62 are wired so that they can be alternatively connected in series and in parallel with a 24 volt power supply. Likewise, the receiving lens heaters 64 and 66 can alternatively be connected in series and in parallel with the power supply. The heaters 60–66 can therefore produce either 1.2 or 4.8 watts per lens. Further adjustment to the heating elements can be achieved by varying the supply voltage.

Figure 5:
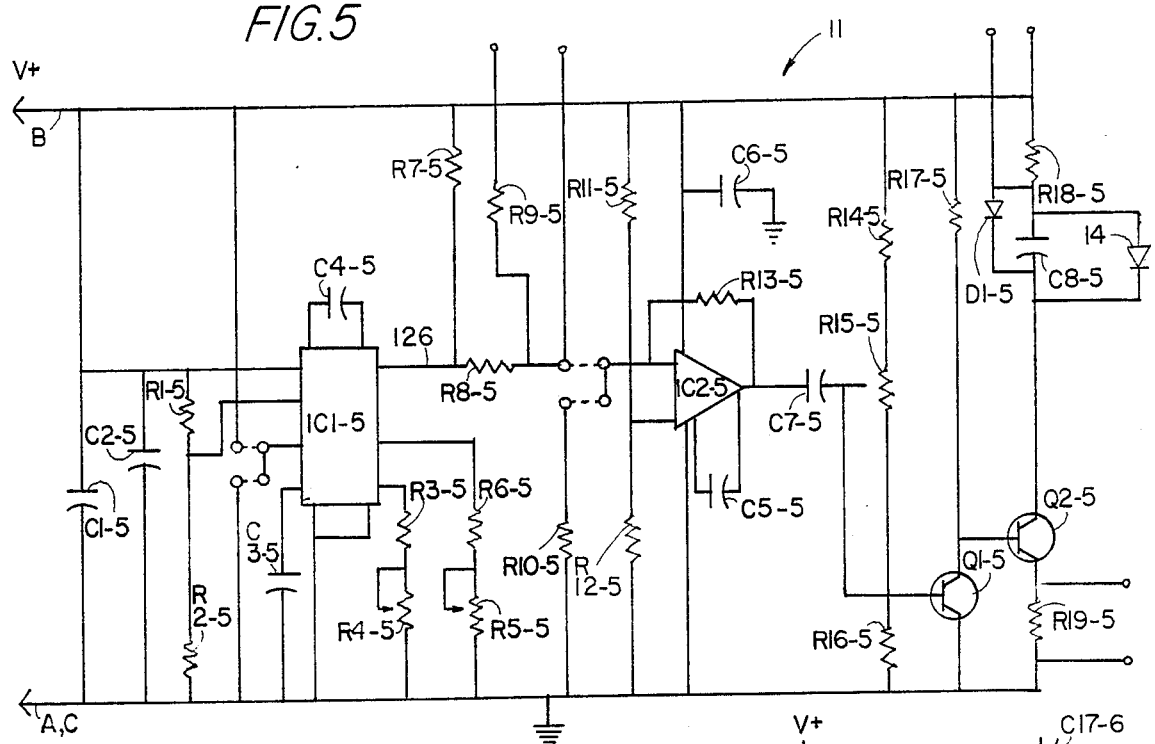
FIG. 5 is a schematic diagram of the transmitter of the embodiment of FIG. 1.

The transmitter 11 consists of a transmitter module, which contains the partially coherent light beam source 12 and the emitter electronics, the transmit modulator printed circuit board for the modulator 13, and a separate power supply. FIG. 5 is a schematic diagram of the electronic circuitry of the transmitter 15. Power is provided from the power supply on lines B, and A,C. The transmitter voltage controlled oscillator IC1-5 is adjusted to produce a nominal square wave output of a 50% duty cycle at a frequency of 50 kilohertz. The output from the voltage controlled oscillator IC1-5 is provided on line 126 and is passed to a buffer amplifier IC2-5. The variable resistor R4-5 is used to fine tune the frequency of the output of the voltage controlled oscillator IC1-5. The output of the buffer amplifier IC2-5 is connected to a variable resistor R15-5 which is tuned to adjust the current provided to power the IRED 14. The transistors Q1-5 and Q2-5 boost power to drive the IRED 14. The diode D1-5 and the capacitor C8-5 prevent a current surge which could damage the IRED 14. Test points in all of the schematic drawings are indicated by taps terminating in small circles.

The IRED 14 is preferably a GE/F5E1 infrared emitter, which is rated 12 milliwatts CW at 880 nanometers. The die size through which light is directed to the lens 20 is 0.4 millimeters square. The drive current to the IRED 14 is adjusted to 100 milliamperes.

Figure 3:
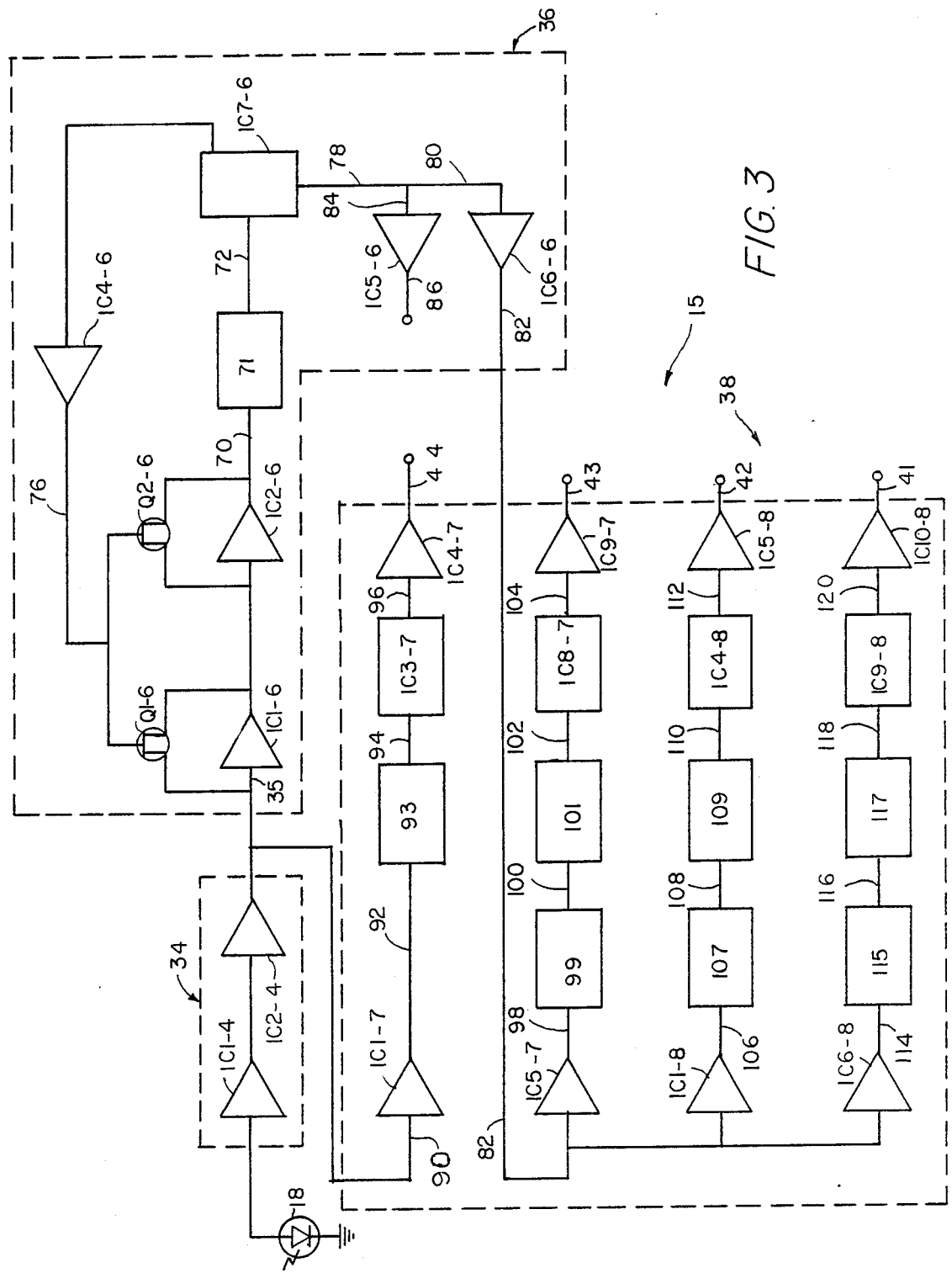
FIG. 3 is a more detailed block diagram of the embodiment of FIG. 1.

The receiver 15 physically consists of the receiver means 16 which is housed in a head or module, the preamplifier 34 and the automatic gain controlled receiver 36. In addition, the signal processor 38 may be considered as part of the receiver 15. FIG. 3 is a functional block diagram of the receiver 15.

The PIN photodiode 18 may be a Litronix BPX61 PIN photodiode, which has an active area of 2.7 millimeters square. This active area is greater than that of the IRED 14. The larger incoherency half angle in the photosensitive receiver means 16 is not as critical as that of the IRED 14, and it is desireable to have the larger die so as to avoid possible signal fluctuations caused by vibration of the mount. If the die of the PIN photodiode 18 were relatively small, the system would be more difficult to optically align.

As illustrated in FIG. 3, the output of the PIN photodiode 18 is coupled to the preamplifier 34 which includes a low noise, current to voltage amplifier IC1-4. The preamplifier schematic is illustrated in FIG. 4. The output of amplifier IC1-4 is provided as an input to a gain amplifier IC2-4, which increases the signal by a factor of 10.

Figure 6:
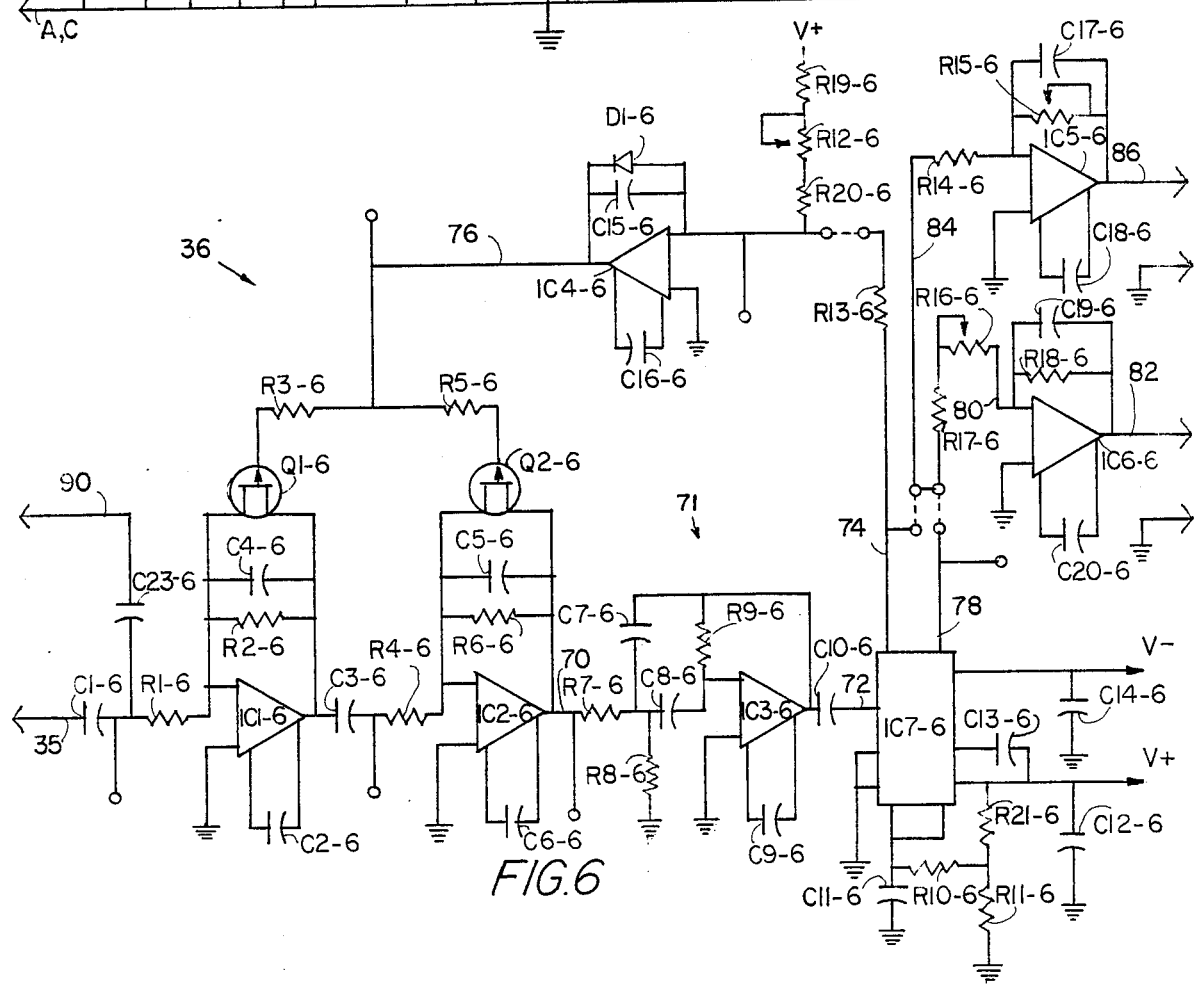
FIG. 6 is the schematic diagram of the automatic gain control receiver of the embodiment of FIG. 1.

From the preamplifier 34, the amplified signal is passed on line 35 to the automatic gain controlled receiver 36, also depicted in FIG. 3. FIG. 6 is the schematic diagram for the automatic gain controlled receiver 36. The input signal from the preamplifier 34 appears on line 35 and is passed to sequentially coupled, FET controlled gain amplifiers IC1-6 and IC2-6. Each of the amplifiers IC1-6 and IC2-6 amplifies the signal by a factor of 20. The amplifiers IC1-6 and IC2-6 are respectively controlled by field effect transistors Q1-6 and Q2-6. The output of amplifier IC2-6 appears on line 70 and is directed to a band pass filter 71 which includes a filtering amplifier IC3-6. The filtering amplifier IC3-6 cleans up the carrier signal. The output of amplifier IC3-6 is provided as an input on line 72 to a root mean square to direct current voltage converter IC7-6 which filters out the 50 kilohertz carrier frequency, but passes the lower frequency signals attributable to scintillations detected by the receiver 15.

The converter IC7-6 provides several outputs. The linear output on line 74 is directed to an integration circuit including an integrating amplifier IC4-6. The output of integrating amplifier IC4-6 appears on line 76 and controls the gates of field effect transistors Q1-6 and Q2-6. The converter IC7-6 also provides a logrithmic output on line 78 which serves as a demodulator signal. The logrithmic output on line 78 is scaled by two amplifiers IC5-6 and IC6-6. The signal on line 78 is provided as an input on line 80 to operational amplifier IC6-6, which provides an output signal on line 82 to the signal processor 38. The output 82 of amplifier IC6-6 drives the low, mid and high frequency discrimination circuits in the signal processor 38. The output of the converter IC7-6 is also provided on line 84 to an operational amplifier IC5-6 which provides an output on line 86 which may be used to drive a signal monitoring device, not depicted in FIG. 1. The resistor R12-6 depicted in FIG. 6, is provided to adjust the output amplitude of the carrier signal.

Figure 7:
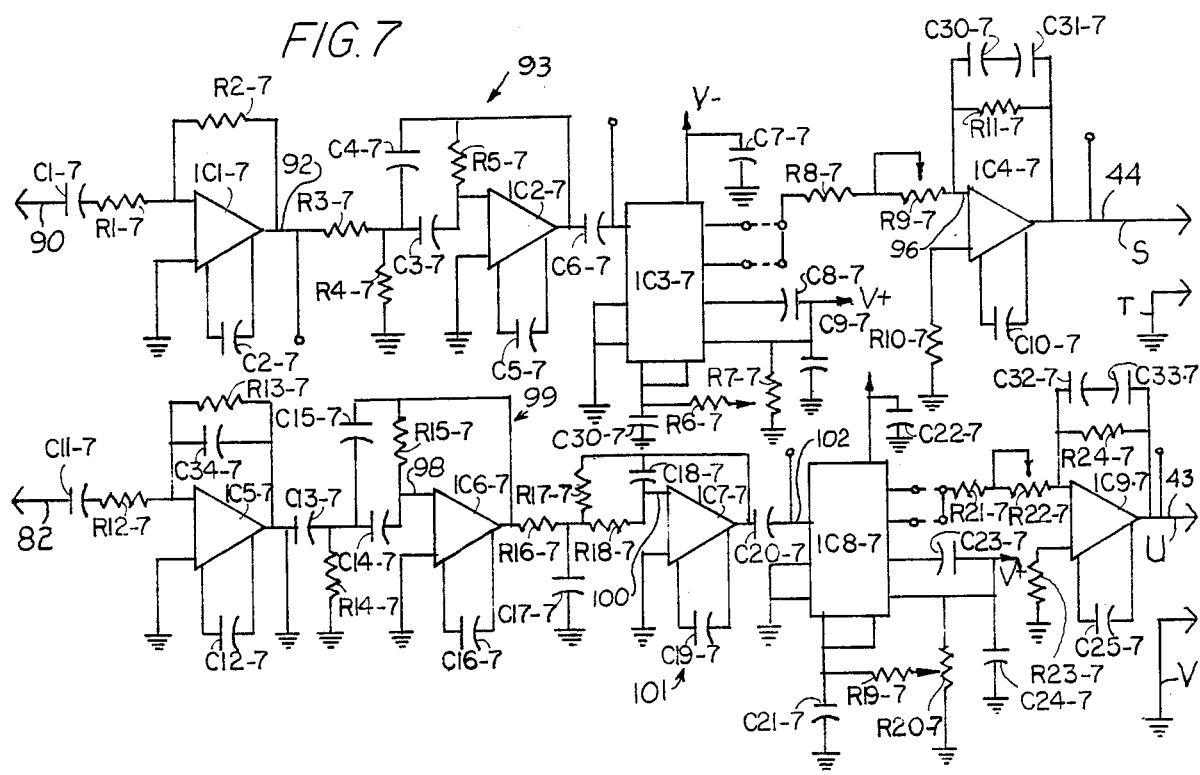
FIG. 7 is a schematic diagram of one of the printed circuit boards of the signal processor of the embodiment of FIG. 1.
Figure 8:
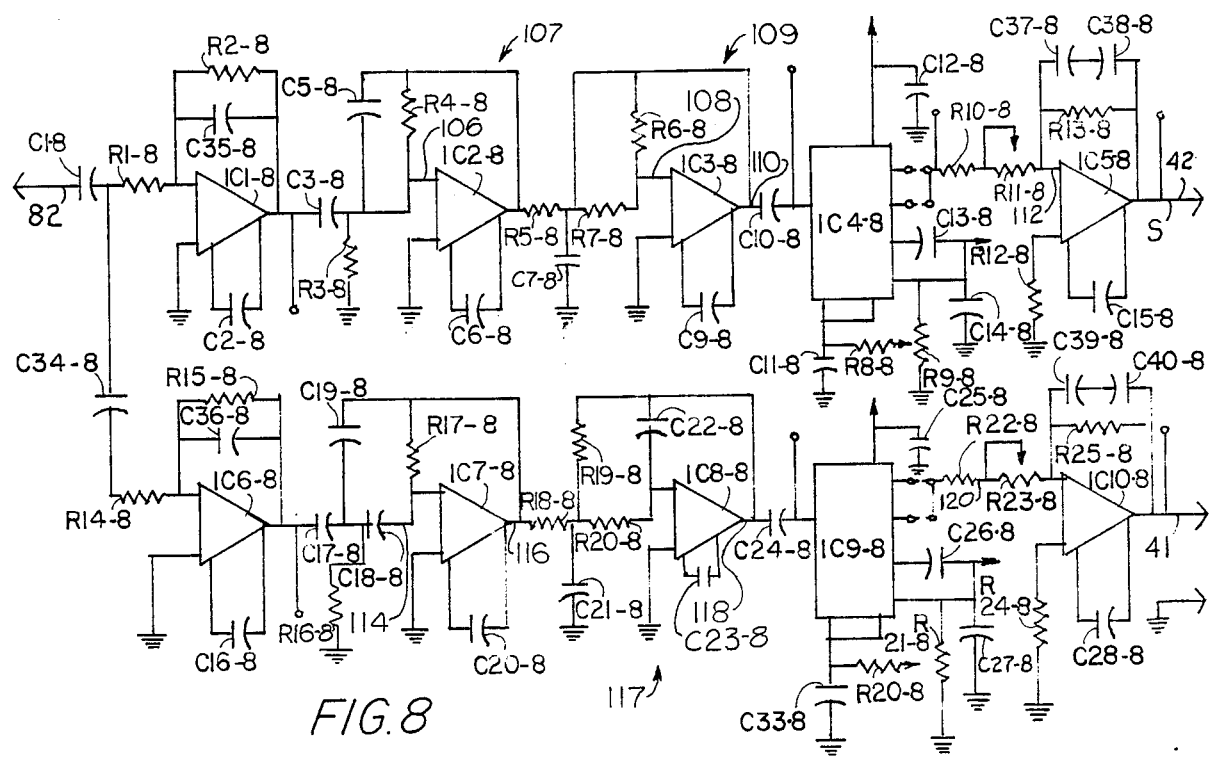
FIG. 8 is a schematic diagram of the other printed circuit board of the signal processor of the embodiment of FIG. 1.

The circuitry of the signal processor 38 is arranged on two circuit boards which are separately depicted in FIGS. 7 and 8. Each of the circuits of FIGS. 7 and 8 contains two channels of filtering and root mean square to direct current conversion. FIG. 3 also illustrates the signal processor 38 in functional block diagram form. The circuitry which produces the high band output 41 and the medium band output 42 is illustrated schematically in FIG. 8. The circuitry which produces the low band output 43 and the carrier output 44 is illustrated in FIG. 7.

With reference to FIGS. 3 and 7, the carrier input on line 90 is directed to a gain stage amplifier IC1-7 which doubles the amplitude of the input signal. The output of amplifier IC1-7 appears on line 92 and is fed as an input to amplifier IC2-7 which functions as the dynamic component of a 50 kilohertz band pass filter 93. The output of amplifier IC2-7 on line 94 is fed as an input to a root mean square to direct current voltage converter IC3-7. The output of converter IC3-7 is provided as an input on line 96 to an integrating amplifier IC4-7. The voltage on the output line 44 is used to monitor the system for major failures, such as a dead transmitter, a disabled preamplifier, or an obstruction in the beam path. The magnitude of the output on line 44 represents the log of the carrier signal.

The log output on line 82 of the automatic gain controlled receiver 36 is applied to the input to the low, mid and high channels of the signal processor 38 through separate buffer amplifiers. Line 82 is connected as an input to the low channel buffer amplifier IC5-7, depicted in FIG. 7. The output of buffer amplifier IC5-7 is provided as an input to a high pass amplifier IC6-7 which is part of a high pass filter 99 on line 98. The output 100 from amplifier IC6-7 is provided as an input to a low pass amplifier IC7-7 which is part of a low pass filter 101. The output of low pass amplifier IC7-7 is provided as an input on line 102 to the root means square to DC voltage converter IC8-7. The log output on line 104 from the converter IC8-7 is provided as an input to an integrating amplifier IC9-7, which has a 10 second time constant. The log output of the converter IC8-7 is used to improve the overall dynamic range of the system. The output of the integrating amplifier IC9-7 on the low channel line 43 is a voltage which is the log of the low channel signal. The overall gain of the low channel signal, from line 82 to line 43 is a factor of 10.

Signal processing circuitry corresponding to that used to derive the low channel output on line 43 is also utilized to provide the medium channel output on line 42 and the high channel output on line 41. The circuitry is depicted in detail in FIG. 8. Specifically, the log output on line 82 from the automatic gain controlled receiver 36 is directed as an input to a buffer amplifier IC1-8. The output of buffer amplifier IC1-8 appears on line 106 as an input to a high pass filter 107 which includes the high pass filtering amplifier IC2-8. Amplifier IC2-8 passes all frequencies above 250 hertz. The output of amplifier IC2-8 is provided as an input on line 108 to a low pass filter 109 which has a low pass amplifier IC3-8. Amplifier IC3-8 passes only those frequencies below one kilohertz on output line 110. A root mean square to direct current converter IC4-8 provides a log output on line 112 as an input to integrating amplifier IC5-8. Integrating amplifier IC5-8 has a 10-second time interval and produces an output on line 42 which is the log of the medium channel. That is, the output on line 42 is representative of the rate of scintillations occurring at frequencies of between 250 hertz and 1 kilohertz. The overall gain of the mid channel output 43 from the input on line 82 is a factor of 100.

Similarly, the input on line 82 is directed to a buffer amplifier IC6-8 which produces an output on line 114 to a high pass amplifier IC7-8 within a high pass filter 115. High pass amplifier IC7-8 passes frequencies above 1 kilohertz as an output on line 116. This output is provided as an input to a low pass filtering amplifier IC8-8 of the low pass filter 117, which passes outputs on line 118 which are below an upper limit of 4 kilohertz. Line 118 is connected as an input to the root mean square to direct current converter IC9-8, the output line 120 of which is connected as an input to integrating amplifier IC10-8, which also has a 10 second time constant. The output of amplifier IC10-8 is the log of high frequency scintillations in the range of between 1 and 4 kilohertz. The overall gain of the high channel output 41 from the input on line 82 is a factor of 1000.

FIG. 9 illustrates the power connections for the IC circuits identified in Table 2. FIG. 10 illustrates the power connections for those amplifiers listed in Table 3. The capacitors Cb each have values of 0.1 microfarads. These capacitors aid in cleaning up power inputs to the amplifiers listed in Table 3.

The values and component identifications for the circuit elements depicted in FIG. 4 are listed in Table 4. Similarly the values and component identifications of the circuit elements depicted in FIGS. 5, 6, 7 and 8 are correspondingly listed in Tables 5, 6, 7 and 8.

FIG. 11 is a diagram illustrating the circuitry utilized to power the lens heaters 60, 62, 64 and 66. The circuitry is identical for both the transmitter lens heaters 60 and 62 and the receiver lens heaters 64 and 66 Therefore, only the circuitry depicting the receiver lens heaters 64 and 66 is illustrated in FIG. 11.

Positive 24 volt power is supplied on line 120 to a plug indicated at P6. The common, return line to the electrical power supply is indicated at 122. The plug P6 is a plastic coupling which includes a key receptacle P6K in one corner. The key P6K receptacle or cavity is configured to receive a stud-like key J6K that projects from a jack J6 adapted to be coupled to the plug P6. Alignment of the key J6K with the key receptacle P6K is necessary to ensure that the plug P6 may be connected in only a selected manner to the corresponding jack J6. The jack J6 includes electrical connections to the lens heating elements 64 and 66. In FIG. 4 the key P6K is positioned so that when the jack J6 is physically connected to the plug P6, the electrical heaters 64 and 66 are connected in parallel to the power lines 120 and 122.

As previously noted, the heaters 64 and 66 may be connected in series. To effectuate such a coupling, the key J6K is removed from the upper left hand corner of the jack J6 and is reinserted into the lower right hand corner of the jack J6. When the key J6K is moved in this manner, the jack J6 must be rotated 180 degrees from the position indicated in FIG. 11 in order to fit into the plug P6. When the plug P6 and the jack J6 are coupled together in this manner, the heaters 64 and 66 are connected in series.

FIG. 11 also illustrates an optional de-icer 126 which includes a thermostat 128. The thermostat 128 closes at 35 degrees Fahrenheit and opens at 45 degrees Fahrenheit. The de-icer 126 is electrically connected through a jack J7 which includes a key J7K. The key J7K fits into the key receptacle P7K in a plug P7. The de-icer plug P7 is connected in parallel with the lens heating plug P6 to receive power from the direct current power lines 120 and 122.

The plug and jack connections for the electrical heaters and the de-icer are necessary due to the physical attachment of the heating elements to the focusing lenses. By providing the jack J6 with a reversible key J6K, the electrical heaters may be, at the option of the user, alternatively connected in parallel or in series.

Undoubtedly, numerous variations and modifications of the invention will become readily apparent to those familiar with conventional optical weather identification systems. Accordingly, the scope of the invention should not be construed as limited to the specific embodiment thereof depicted and described herein, but rather is defined in the claims appended hereto.

TABLE 1

| Plot Line | Rain Rate (mm/h) |
|---|---|
| 50 | 0.1 |
| 51 | 1.0 |
| 52 | 10.0 |
| 53 | 100.0 |

TABLE 2

| IC2-4, | | |
|---|---|---|
| IC1-6, | IC2-6, | IC5-6, |
| IC2-7, | IC5-7, | IC6-7, |
| IC1-8, | IC3-8, | IC6-8, |
| IC8-8 | | |

TABLE 3

| IC1-4, | | |
|---|---|---|
| IC3-6, | IC4-6, | IC6-6, |
| IC1-7, | IC4-7, | IC7-7, |
| IC2-8, | IC5-8, | IC7-8, |
| IC9-7, | IC10-8 | |

TABLE 4

| IC1-4 | OP12 |
|---|---|
| IC2-4 | LM101 |
| R1-4, | 221K Ohms |
| R4-4, R5-4 | 2.7 Ohms, ¼ Watts |
| R2-4 | 20K Ohms |
| R3-4 | 100K Ohms |
| C4-4, C5-4, C7-4, C6-4 | 10 Microfarads |
| C1-4, C2-4 | 5 Picofarads |
| C9-4, C3-4 | 15 Picofarads |
| C8-4 | .01 Microfarads |

TABLE 5

| IC1-5 | XR2207 |
|---|---|
| IC2-5 | LM101 |
| D1-5 | IN270 |
| Q1-5 | 2N2905 |
| Q2-5 | 2N4919 |
| R18-5, R19-5 | 10 Ohms, 5 Watts |
| R17-5 | 150 Ohms, ½ Watt |
| R14-5 | 1K Ohms |
| R10-5, R8-5, R9-5 | 20K Ohms |
| R3-5, R6-5, R15-5 | 10K Ohms |
| R1-5, R7-5, R13-5 5 | .1K Ohms |
| R2-5, R16-5 | 4K Ohms |
| R4-5, R5-5, R12-5 | 100K Ohms |
| R11-5 | |
| C8-5 | 0.01 Microfarads |
| C5-5 | 15 Picofarads |
| C1-5 | 100 Microfarads |
| C2-5, C6-5, C7-5 | 0.1 Microfarads |
| C3-5 | 1.0 Microfarads |
| C4-5 | 470 Picofarads |

TABLE 6

| IC1-6, IC2-6, IC6-6, IC3-6, IC4-6, IC5-6 | LM101 |
|---|---|
| IC7-6 | AD536 |
| Q1-6, Q2-6 | 2N3820 |
| D1-6 | IN270 |
| R21-6, R11-6 | 24.9K Ohms |
| R8-6, R17-6 | 1K Ohms |
| R1-6 | 5.11K Ohms |
| R16-6 | 2K Ohms |
| R13-6 | 68K Ohms |
| R2-6, R6-6, R10-6 | 221K Ohms |
| R3-6, R5-6, R18-6, R15-6 | 100K Ohms |
| R20-6, R19-6 | 6.81K Ohms |
| R12-6 | 1 Megohm |
| R4-6, R14-6 | 10K Ohms |
| R7-6 | 9.53K Ohms |
| R9-6 | 95.3K Ohms |
| C1-6, C23-6, C3-6 | .01 Microfarads |
| C10-6, C4-6, C5-6 | 5 Picofarads |
| C20-6, C18-6, | 100 Picofarads |
| C21-6, C22-6 | 100 Microfarads |
| C13-6 | .033 Microfarads |
| C12-6, C14-6 | 0.1 Microfarads |
| C2-6, C6-6, C9-6, C16-6 | 15 Picofarads |

TABLE 6-continued

| C7-6, C8-6 | 330 Picofarads |
|---|---|
| C17-6 | 470 Picofarads |
| C11-6 | .001 Microfarads |
| C19-6 | 390 Picofarads |
| C15-6 | 10 Microfarads |

TABLE 7

| IC1-7, IC2-7, IC4-7 IC5-7, IC6-7, IC9-7 | LM101 |
|---|---|
| IC3-7, IC8-7 | AD536 |
| R18-07 | 40.2K Ohms |
| R15-7 | 133K Ohms |
| R14-7 | 30.1K Ohms |
| R10-7, R23-7 | 3.01K Ohms |
| R9-7, R22-7 | 2K Ohms |
| R5-7 | 9.53K Ohms |
| R16-7, R17-7 | 80.4K Ohms |
| R4-7 | 1K Ohms |
| R6-7, R11-7, R13-7 | 221K Ohms |
| R19-7, R24-7 | |
| R2-7, R12-7 | 20K Ohms |
| R25-7, R26-7 | 2.2 Ohms, 2 Watts |
| R1-7, R8-7, R21-7 | 51.1K Ohms |
| R7-7, R20-7 | 50K Ohms |
| C30-7, C31-7 | 100 Microfarads |
| C30-7, C34-7, C21-7 | .001 Microfarads |
| C7-7, C9-7, C13-7, C14-7 | 0.1 Microfarads |
| C15-7, C22-7, C24-7 | |
| C1-7, C6-7, C20-7 | 0.01 Microfarads |
| C2-7, C5-7 | .15 Picofarads |
| C3-7, C4-7, C10-7 | 330 Picofarads |
| C25-7 | |
| C8-7, C23-7, C32-7, C33-7 | 100 Microfarads |
| C26-7, C27-7, C28-7, C29-7 | |
| C11-7 | 1 Microfarads |
| C12-7 | 100 Picofarads |
| C16-7, C19-7 | 150 Picofarads |
| C17-7 | .022 Microfarads |
| C18-7 | .0056 Microfarads |

TABLE 8

| IC1-8, IC2-8, IC3-8, IC5-8, IC6-8, IC7-8, IC8-8, IC10-8 | LM101 |
|---|---|
| IC4-8, IC9-8 | AD536 |
| R19-8 | 28.0K Ohms |
| R20-8 | 2.55K Ohms |
| R16-8 | 3.24K Ohms |
| R8-8, R13-8, R15-8 | 221K Ohms |
| R20-8, R25-8 | |
| R7-8 | 2.18K Ohms |
| R17-8 | 71.5K Ohms |
| R4-8 | 133K Ohms |
| R18-8 | 280K Ohms |
| R1-8, R2-8, R14-8 | 20K Ohms |
| R3-8, R12-8 | 30.1K Ohms |
| R6-8 | 24K Ohms |
| R5-8 | 2.4K Ohms |
| R10-8, R22-8 | 51.1K Ohms |
| R11-8, R23-8 | 2K Ohms |
| R9-8, R21-8 | 50K Ohms |
| R24-8 | 3.01K Ohms |
| C1-8, C12-8, C14-8 C34-8, C27-8, C25-8 | .1 Microfarads |
| C35-8, C36-8 | .180 Picofarads |
| C5-8, C3-8, C4-8, C10-8 C24-8 | 0.01 Microfarads |
| C2-8, C6-8, C9-8, C16-8 C20-8, C23-8 | 100 Picofarads |
| C7-8, C17-8, C18-8 | .033 Microfarads |
| C13-8, C26-8 | 10 Microfarads |
| C11-8, C22-8, C33-8 | .001 Microfarads |
| C15-8, C28-8 | 15 Picofarads |
| C37-8, C38-8, C39-8, C40-8 | 100 Microfarads |
| C19-8 | .0033 Microfarads |
| C21-8 | .022 Microfarads |

I claim:

1. A weather identification system comprising a partially coherent light beam source, photosensitive receiver means positioned a predetermined distance from said partially coherent light beam source and in optical communication therewith to produce electronic signals in response to scintillations caused by particle movement between said source and said receiver means, wherein the product of said predetermined distance and one-half the angle of incoherency of said partially coherent light beam source is no greater than about 2.5 millimeters, automatic gain control means coupled to said receiver means, signal processing means coupled to said automatic gain control means for producing first, second and third separate outputs for detected scintillations wherein said first output has a frequency range above about one kilohertz characteristic of rain, said second output has a frequency range lower than that of said first output and characteristic of both rain and snow, and said third output has a frequency range lower than both said first and second outputs and characteristic of snow and including frequencies below about 250 hertz.

2. A weather identification system according to claim 1 wherein said first output has a frequency range above about one kilohertz, said second output has a frequency range of between about 250 hertz and about one kilohertz, and said third output has a frequency range below about 250 hertz.

3. A weather identification system according to claim 1 wherein said partially coherent light beam source is comprised of an infrared light emitting diode.

4. A weather identification system according to claim 3 wherein said partially coherent light beam source is further comprised of a 175 millimeter achromatic transmitter lens having a focal ratio of F3.5.

5. A weather identification system according to claim 4 wherein said photosensitive receiver means is comprised of a 175 millimeter achromatic receiver lens having a focal ratio of F3.5, a mask defining a horizontal slot about one millimeter in height located behind said receiver lens, an infrared filter located behind said mask, and a photodiode detector.

6. A weather identification system according to claim 5 further comprising electrically powered heating means for both of said lenses.

7. A weather identification system according to claim 6 wherein each of said heating means is comprised of a pair of heaters arranged for alternative connection in series and in parallel with said power supply.

8. A weather identification system according to claim 1 wherein said light beam source is driven at a carrier frequency of at least about 10 kilohertz, and said automatic gain control means includes a plurality of amplification stages and a root mean square to direct current converter which produces a linear output to said amplification stages whereby said amplification stages are controlled by said carrier frequency, and said converter also produces a logrithmic output to said signal processing means, and said signal processing means includes first, second and third band pass filters coupled to receive said logrithmic output of said automatic gain control means and to respectively generate said first, second and third outputs.

9. A weather condition indicating system comprising: a partially coherent light beam generating transmitter, an optical receiver located in optical communication with said transmitter and in spaced separation therefrom such that the product of one-half the angle of incoherency of said light beam multiplied by the distance of separation of said transmitter and said receiver is no greater than about 2.5 millimeters, automatic gain control means coupled to amplify signals from said receiver generated in response to scintillations occurring in said light beam from said transmitter, and signal processing means for separately isolating signals from said receiver having frequencies characteristic of rain, snow and air without precipitation 10. A weather condition indicating system according to claim 9 further characterized in that said spaced separation of said transmitter and said receiver is about one meter.

11. A weather condition indicating system according to claim 10 further characterized in that said product of one-half said angle of incoherency multiplied by said distance of separation is about 1.1 millimeters.

12. A weather condition indicating system according to claim 9 wherein said signal processor further comprises frequency discrimination means to separate signals having frequencies above one kilohertz, signals having frequencies between about 250 hertz and one kilohertz, and signals having frequencies below about 250 hertz.

13. A weather condition indicating system according to claim 9 further characterized in that said transmitter is comprised of an infrared light emitting diode.

14. A weather condition indicating system according to claim 13 wherein said transmitter is further comprised of a focusing lens which produces a partially coherent light beam about 50 millimeters in diameter.

15. A weather condition indicating system according to claim 9 in which said transmitter is driven by a carrier signal generator and said signal processing means is comprised of four channels of filtering and root mean square to direct current converter means which separately isolate signals from said receiver as aforesaid and said signal processing means also includes means to monitor the carrier signal from said carrier signal generator.

16. A weather condition indicating system according to claim 9 in which said transmitter and said receiver are both equipped with focusing lenses and further comprising electrical heating means for heating both of said lenses.

* * * * *